United States Patent [19]

Allgood et al.

[11] Patent Number: 5,176,651

[45] Date of Patent: Jan. 5, 1993

[54] COMBINATION SURGICAL TROCAR HOUSING AND SELECTIVE REDUCER SLEEVE ASSEMBLY

[75] Inventors: Fred A. Allgood, Fort Worth; Michael W. Freitas, Irving, both of Tex.

[73] Assignee: Dexide, Inc., Fort Worth, Tex.

[21] Appl. No.: 678,686

[22] Filed: Apr. 1, 1991

[51] Int. Cl.⁵ .............................................. A61M 5/00
[52] U.S. Cl. .................................... 604/167; 604/164
[58] Field of Search ............... 604/164, 166, 167, 158, 604/157

[56] References Cited

U.S. PATENT DOCUMENTS

| | | | |
|---|---|---|---|
| 3,097,646 | 7/1963 | Scislowicz | 604/167 |
| 3,406,685 | 10/1968 | May | 604/164 |
| 4,581,019 | 4/1986 | Gurelarv et al. | 604/164 |
| 4,585,440 | 4/1986 | Tchervenkov et al. | 604/167 |
| 4,673,393 | 6/1987 | Suziki et al. | 604/167 |
| 4,758,225 | 7/1988 | Cox et al. | 604/167 |
| 4,824,433 | 4/1929 | Marz et al. | 604/164 |
| 4,909,798 | 3/1990 | Fleischhacker et al. | 604/167 |
| 4,960,412 | 10/1990 | Fink | 604/167 |
| 4,966,587 | 10/1990 | Baumgart | 604/167 |
| 5,009,643 | 4/1991 | Reich et al. | 604/167 |
| 5,030,206 | 7/1991 | Lander et al. | 604/164 |
| 5,041,095 | 8/1991 | Littrell | 604/167 |
| 5,062,936 | 11/1991 | Wendell | 604/167 |

*Primary Examiner*—Paul J. Hirsch
*Attorney, Agent, or Firm*—Jackson & Walker

[57] ABSTRACT

The invention provides a combination surgical trocar housing and selective reducer sleeve assembly in which the sleeve assembly members may be telescopically received within the trocar housing to reduce the diameter therethrough. The sleeve members provide a seal to prevent transmission of fluid within the annular area between internal and external diameters of respective members and may be latchingly secured relative to one another to resist telescopic expansive movement to stabilize the sleeve assembly relative to the trocar housing. The sleeve assembly permits acceptance through a single trocar housing of a number of auxiliary surgical instruments having serially smaller diameters, thus enabling performance of the surgical operation using each such instrument, without removal from the body wall of the original trocar housing.

35 Claims, 3 Drawing Sheets

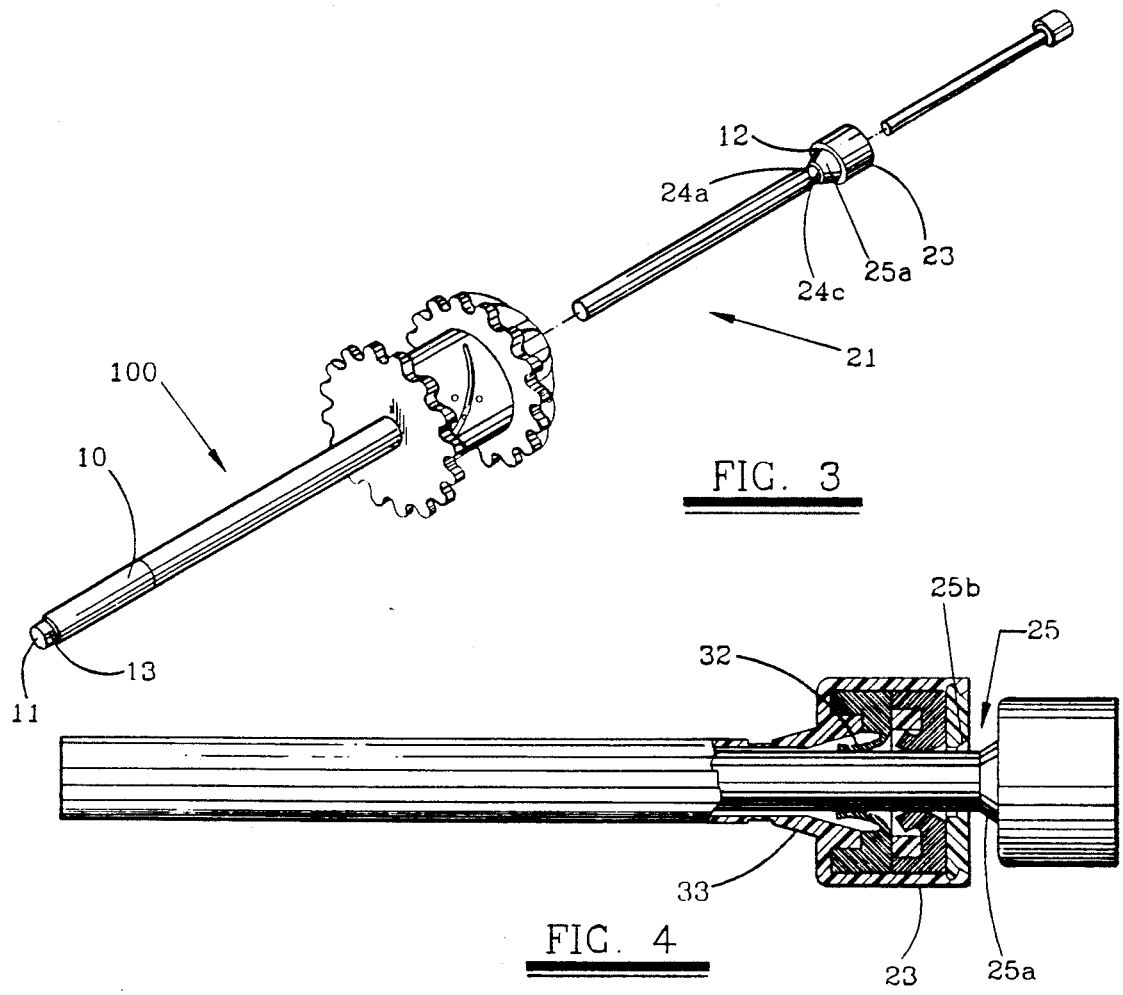
FIG. 3
FIG. 4
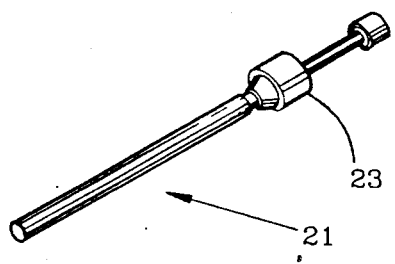
FIG. 5

COMBINATION SURGICAL TROCAR HOUSING AND SELECTIVE REDUCER SLEEVE ASSEMBLY

BACKGROUND OF THE INVENTION (1) Field of the Invention

The invention relates to a combination surgical trocar housing and selective reducer sleeve assembly.

(2) Brief Description of the Prior Art

Surgical endoscopic procedures typically follow three steps. First, a cannula, such as a Veress cannula, is inserted through the abdominal cavity through the abdominal wall and the cavity is inflated with insufflating gas which is passed through the cannula tubular housing. After insufflating, a small incision is made in the skin and a standard trocar spike is thrust into the inflated abdomen through the bore of the trocar tube. The spike is inserted for purposes of puncturing or cutting of the abdominal wall and piercing the fascia and peritoneum inside the cavity. After removal of the spike, a suction/irrigation cannula is re-inserted through the trocar housing and into the opening so that fluids may be drained from the body cavity.

Endoscopic surgery also includes the introduction through a trocar tube of a number of auxiliary surgical instruments such as, for example, a laparoscope, or the like. It is not uncommon during endoscopic surgical operations to utilize several instruments which are introduced through a particularly sized trocar housing. If the diameter of the respective instruments to be utilized to the surgical operations are not substantially identical for companion sealing receipt within the trocar housing, the trocar housing must be removed from the abdominal cavity position, and replaced with a smaller (or larger) diameter trocar housing for diametric compatability with the respective surgical instruments. Such removal and re-insertion of the trocar housing is time comsuming and further complicates the surgical operation.

The present invention addresses the deficiencies above described in such surgical instruments.

SUMMARY OF THE INVENTION

The present invention is directed to a combination surgical trocar housing and selective reducer sleeve assembly. The device includes an elongated trocar tubular housing of a first internal diameter and having a first open end portion for positioning through a body wall, such as a human abdomen. The trocar tubular housing has an open end portion for introduction and removal of auxiliary surgical devices therethrough, such as an endoscope, while the first open end portion is positioned through the body wall. An insert sleeve assembly is concentrically introducable through the second opposite open end portion of the trocar housing and includes a cylindrical housing of a second external diameter less than the said internal diameter of the trocar housing. Means for placing the sleeve cylindrical housing in a limited telescopically contracted position relative to the trocar housing is also provided, as well as means for selectively securing the sleeve cylindrical housing in the telescopically contracted position.

The device may also include a first seal means for sealing the opening through the outboard-most end of the cylindrical housing, the seal means being formed of a resilient material, such as an elastomer, having a concave curvature facing the first open end portion of the trocar tubular housing, as well as a slit formed through the seal to define first and second seal lips facing each other and placable in sealing relationship around the exterior of the sleeve as the sleeve housing is placed through the trocar tubular housing. The lips move into sealing contact with one another when the sleeve housing is not therebetween to seal the opening of the sleeve housing. Second seal means are provided outboard of the first seal means for sealing around the sleeve housing as the sleeve housing is placed through the trocar tubular housing.

Thus, the invention provides a sleeve assembly for selective sealing placement interior of the trocar housing through which the auxiliary surgical instruments may be introduced, without removal and reinsertion of the trocar housing. Thus, the invention compensates for diameter variations of various surgical instruments for acceptance and use within only one trocar housing while, at the same time, providing a seal to prevent fluid flow from, for example, the interior to the exterior of the trocar housing, and through the annular area defined between the surgical instrument and the respective sleeve member and/or trocar housing.

BRIEF DESCRIPTION OF THE DRAWINGS

FIG. 3 is an isometric view of the trocar housing with a series of first and second sleeve members being positioned for introduction into the trocar housing.

FIG. 4 is a partial sectional view of a sleeve member illustrating portions of the latching members, as well as the seal means for sealing against the external diameter of a second sleeve member introduced therethrough.

FIG. 5 is an isometric view showing the exterior of first and second sleeve members with the second or smaller member being telescopically received within the first or larger member.

DESCRIPTION OF THE PREFERRED EMBODIMENTS

Figure 1:
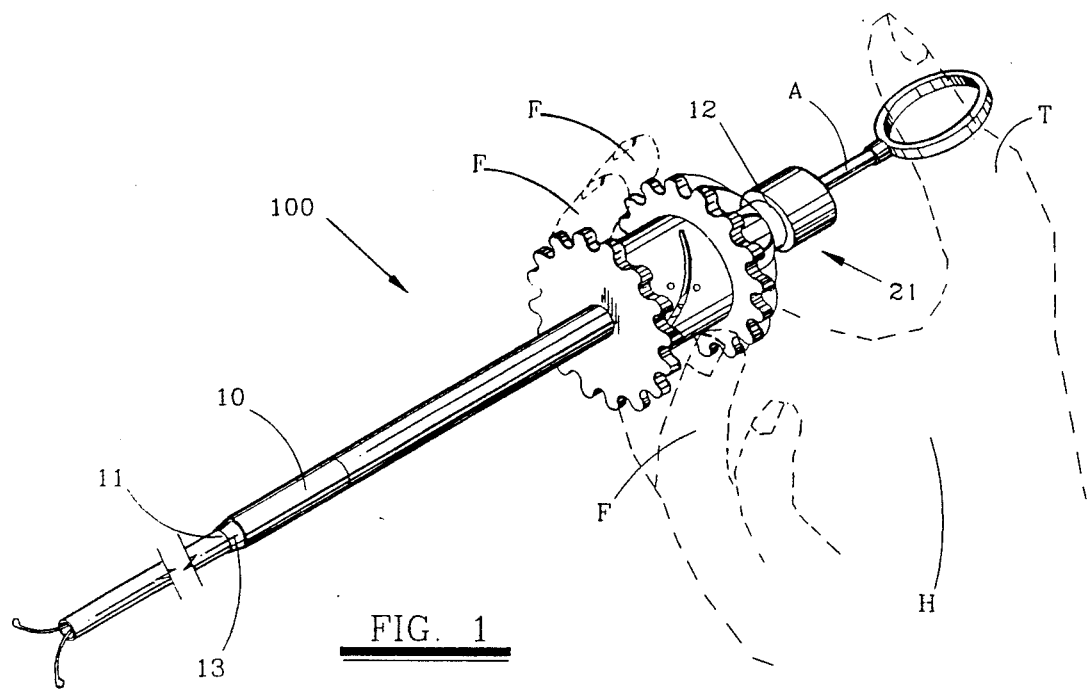
FIG. 1 is an isometric view of the device of the present invention held in the hand of a surgeon with an auxiliary surgical device being disposed therethrough.

With first reference to FIG. 1, there is shown the apparatus of the present invention 100 in isometric view with an auxiliary surgical device A being disposed through a trocar housing 10 concentrically receiving a sleeve cylindrical housing 21. The trocar housing 10 is held in position for introduction into the body walls, such as an abdomen, for performance of surgical procedures, and is held in the position, as shown, in a surgeon's hand H, between fingers F, with the surgeon's thumb T controlling the movement of the auxiliary surgical device A or in the palm of the surgeon.

The trocar housing 10 has a first open end 11 for insertion into the abdomen or other body wall (prior to introduction of the auxiliary surgical device A through the trocar housing 10), and a second open end 12 through which is received the sleeve housing 21, as shown. The trocar housing 10 has an internal diameter 13.

Figure 2:
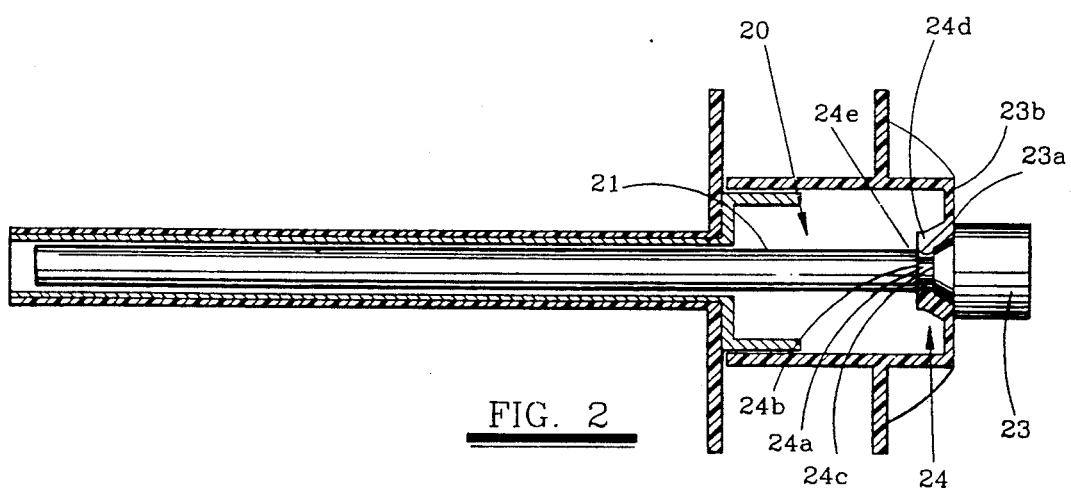
FIG. 2 is a cross sectional view schematically illustrating the trocar housing of the present invention accepting a sleeve housing therethrough.

As shown in FIG. 2, a sleeve assembly 20 includes a sleeve cylindrical housing 21 shown concentrically received through the internal diameter 13 of the trocar housing 10. The sleeve cylindrical housing 21 has an outer diameter 22 (FIG. 4) smaller than the internal diameter 13 of the trocar housing 10 At the outboard most end of the sleeve cylindrical housing 21 is a cap portion 23 having an outer diameter larger than the diameter of the second open end 12 of the trocar housing 10 such that the inwardly facing face 23a of the cap port-ion 23 will come into abutting relationship with a companion frontal housing 23b of the trocar housing 10 when the sleeve cylindrical housing 21 is concentrically received within the trocar housing 10 to limit telescopic contraction of the sleeve housing 21 relative to the trocar housing 10.

Means for selective securement 24 are provided to secure the sleeve cylindrical housing 21 relative to the trocar housing 10 in telescopically contracted position and includes a snap groove 24a profiled around the sleeve cylindrical housing 21 and providing inner and outer shoulders 24b, 24c for receipt of a latch head portion 24e of a circumferentially extending flexible latch finger or ring 24d circumscribed interiorly within the trocar housing 10 outer most end and interior of the frontal housing 23b. Thus, as the sleeve cylindrical housing 21 is introduced into the trocar housing 10, the flexible latch fingers 24d will be biased radially outwardly, somewhat, as they pass around the outer diameter 22 of the sleeve cylindrical housing 21 until such time as the latch head portions 24e come into alignment with the snap groove 24a, such alignment permitting the flexible latch finger or ring 24d to radially contract to its normal radius and flex inwardly within the groove 24a such that the interengagement of the latch head 24e relative to the shoulder 24b resists telescopic expansion of the sleeve housing 21 relative to the trocar housing 10. Additionally, the interrelationship between the shoulder 24c and the head 24e resists further telescopic contraction of the members 21, 10 relative to one another (alone or in combination with the contact of the face 23a on the frontal housing 23b).

Figure 7:
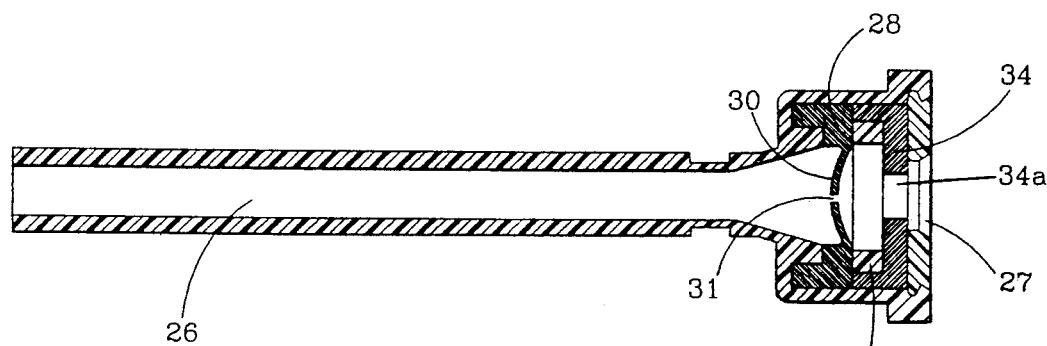
FIG. 7 is a cross-sectional illustration of the sealing means of an alternative sleeve member including means for resisting telescopic expansion subsequent to introduction into another sleeve member.

Now with reference to FIG. 7, the sleeve cylindrical housing 21 is shown with its passageway 26 therein outwardly terminating an opening 27. A first seal means is housed within the cap portion 23 and may be composed of an elastomeric or similar substance and is held in position within the cap portion 23 by means of a doughnut-shaped seal retainer 29 which, in turn, also secures within the cap portion 23 a second seal 34.

Figure 6:
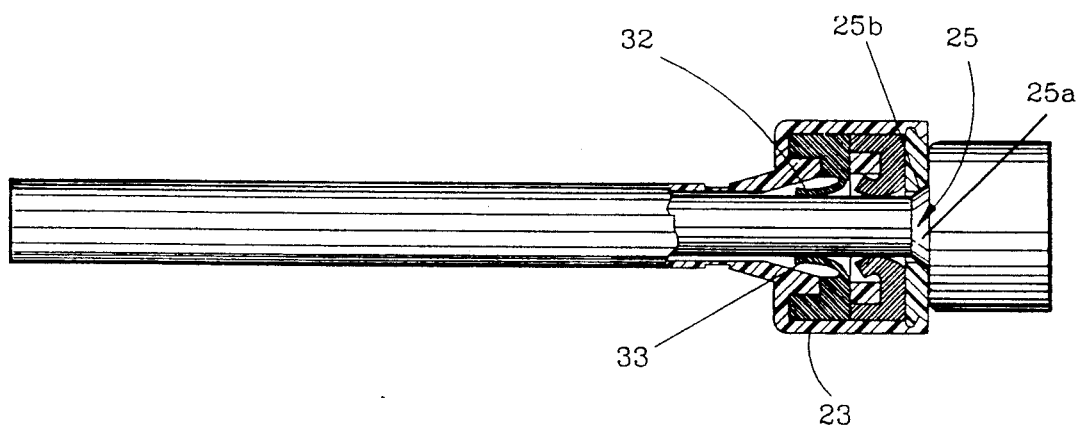
FIG. 6 is a partial sectional view similar to that of FIG. 4, illustrating the second sleeve member being telescopically contractedly placed within the first sleeve member and without means to resist subsequent telescopic expansion.

The first seal means 28 has a concave curvature 30 facing inwardly within the passageway 26. A central slit 31 is provided in the first seal means 28 for defining first and second seal lips 32, 33 (FIG. 6). The second seal means 34 has a small diameter opening 34a such that when a subsequent sleeve cylindrical housing 21 is introduced within the first housing 21, as in FIG. 6, the second seal means will sealingly engage around the exterior diameter of the second sleeve cylindrical housing 21.

Of course, when no device is inserted within the sleeve cylindrical housing 21, the first and second seal lips 32, 33 will come into sealing contact with one another (FIG. 7) to prevent fluid communication across the passageway 26.

In some instances, it may not be necessary for a second or other subsequential sleeve cylindrical housing 21 to be latchingly secured within its sleeve housing 21 or the trocar housing 10. In such instance, a contoured sealing surface 25 may be provided through the opening 27 by means of provision of a conically shaped ring profile 25a on the sleeve housing 21 just inboard of the cap portion 23 for receipt within a respectively bevelled or profiled seal groove element 25b on the cap portion 23 such that the interalignment between the members 25, 25b will provide a relatively tight seal therebetween and will at least satisfactorily resist fluid flow therebetween from the interior of either the trocar housing 10 or the sleeve cylindrical housing 21.

OPERATION

When it is anticipated during a surgical procedure that a plurality of auxiliary surgical devices A will be utilized during the operation, the trocar housing 10 will be introduced into the body cavity such that the first open end 11 is placed therethrough. A sleeve housing 21 may be introduced into the trocar housing 10 prior to or subsequent to such introduction of the housing 10 into the body cavity. Typically, the sleeve housing 21 will not have been previously introduced into the trocar housing 10. After, for example, a trocar spike has been thrust through the housing 10, it will be retrieved therefrom. A sleeve cylindrical housing 21, as described, will be introduced through the second open end 12 of the trocar housing 10 until the latch fingers 24d are then placed within the groove 24a and the cap portion 23 encounters the face 23a. Now, the first and second seal lips 32, 33 will be sealingly engaged around the exterior of the sleeve cylindrical housing 21 and the housing 21 will be latchingly secured within the trocar housing 10 in telescopically retracted position. A deliberate, but slight pull by the surgeon through application of the fingers F onto the cap portion 23 will overcome the interengagement of the latch fingers 24d in the groove 24a to remove the sleeve cylindrical housing 21 from the trocar housing 10, if and when desired.

Subsequent to introduction of the sleeve cylindrical housing 21 into the trocar housing 10, as described, the apparatus 100 will be in position as shown in FIG. 2. Now, the auxiliary surgical device A may be introduced through the cap portion 23 of the sleeve cylindrical housing 21 such that it travels through the opening 27 into the passageway 26 and out the first open end 11 of the trocar housing 10 into the body cavity (FIG. 1).

Subsequent to performing the surgical operating procedure with the auxiliary surgical device A as shown in FIG. such device A may be retrieved from the interior of the sleeve cylindrical housing 21 and a second sleeve cylindrical housing 21 may be introduced through the first sleeve cylindrical housing 21 in similar fashion, as shown in FIGS. 3 and 5.

It will be appreciated that provision of the present apparatus 100 enables the trocar housing 10 which is originally utilized to always remain within the body wall during the entire surgical procedure, while permitting the trocar housing 10 to always be in sealed relation to prevent fluid communication therein between the exterior and the interior thereof, as well as through the respective sleeve cylindrical housings 21. Additionally, it is not necessary for the trocar housing 10 to be removed and a subsequent smaller internal diameter trocar housing reintroduced into the body cavity slit for introduction of second, smaller, auxiliary surgical devices A.

Although the invention has been described in terms of specified embodiments which are set forth in detail, it should be understood that this is by illustration only and that the invention is not necessarily limited thereto, since alternative embodiments and operating techniques will become apparent to those skilled in the art in view of the disclosure. Accordingly, modificatins are contemplated which can be made without departing frm the spirit of the described invention.

What is claimed and desired to be secured by Letters Patent is:

1. A combination surgical trocar housing and selective reducer sleeve assembly, comprising: an elongated trocar tubular housing of a first internal diameter, having a first open end portion for positioning through a body wall, and a second opposite open end portion for introduction and removal of auxiliary surgical devices therethrough while said first open end portion is positioned through the body wall; a reducer sleeve assembly concentrically introducible through said second opposite open end portion of said trocar housing and including a cylindrical housing of a second external diameter less than the said internal diameter of the trocar housing said reducer sleeve assembly having a first inboard open end and a second outboard open end, said first and second open ends permitting introduction and removal of said auxiliary surgical devices into and out of said open ends of said assembly while said assembly is within said trocar housing; means for placing the sleeve cylindrical housing in a limited telescopically contracted position relative to said trocar housing; and mechanical means for selectively securing said sleeve cylindrical housing in said telescopically contracted position.

2. The device of claim 1 further including: means for sealing the area defined by the outer diameter of the sleeve cylindrical housing and the internal diameter of the trocar housing immediate said second opposite open end portion, to prevent fluid flow thereacross.

3. The device of claim 1 further including: means for sealing the area defined by the outer diameter of the sleeve cylindrical housing and the internal diameter of the trocar housing immediate said second opposite open end portion, to prevent fluid flow from the interior of said trocar tubular housing and through said second opposite open end.

4. The device of claim 2 or claim 3, said means for sealing comprising: a circumferentially extending conically shaped ring member on one of said sleeve cylindrical housing and said trocar tubular housing, and a companionly profiled sealing groove defined around the other of said sleeve cylindrical housing and said trocar tubular housing.

5. The device of claim 1, said cylindrical housing having a passageway therethrough communicating with the interior of said trocar tubular housing and terminating in an opening through the outboard most end of said sleeve cylindrical housing for receipt of auxiliary surgical devices therethrough, and further including: a first seal means for sealing said opening, said first seal means being formed of resilient material having a concave curvature facing the first open end portion of said trocar tubular housing; a slit formed through the seal means to define first and second seal lips facing each other and placable in sealing relationship around the exterior of said sleeve housing as said sleeve housing is placed through said trocar tubular housing, said lips moving into sealing contact with one another when said sleeve housing is not therebetween to seal the said opening of said sleeve housing; and second seal means outboard of said first seal means for sealing around said sleeve housing as said sleeve housing is placed through said trocar tubular housing.

6. The device of claim 1 or claim 5, said sleeve cylindrical housing being further adapted to sealingly and latchingly receive a second cylindrical housing of a third exterior diameter less than the said interior diameter of said cylindrical housing.

7. The device of claim 1, wherein said means for selectively securing said sleeve cylindrical housing in said telescopically contracted position comprises: a snap groove defined around the exterior of one of said sleeve cylindrical housing and said trocar tubular housing, and flexible means carried by the other of said sleeve cylindrical housing and said trocar tubular housing, and movable into said snap groove when said sleeve cylindrical housing is in said telescopically contracted position, whereby subsequent telescopic expansive movement of said sleeve cylindrical housing relative to said trocar tubular housing is resisted.

8. The device of claim 2, wherein said means for selectively securing said sleeve cylindrical housing in said telescopically contracted position comprises: a snap groove defined around the exterior of one of said sleeve cylindrical housing and said trocar tubular housing, and flexible means carried by the other of said sleeve cylindrical housing and said trocar tubular housing, and movable into said snap groove when said sleeve cylindrical housing is in said telescopically contracted position, whereby subsequent telescopic expansive movement of said sleeve cylindrical housing relative to said trocar tubular housing is resisted.

9. The device of claim 3, wherein said means for selectively securing said sleeve cylindrical housing in said telescopically contracted position comprises: a snap groove defined around the exterior of one of said sleeve cylindrical housing and said trocar tubular housing, and flexible means carried by the other of said sleeve cylindrical housing and said trocar tubular housing, and movable into said snap groove when said sleeve cylindrical housing is in said telescopically contracted position, whereby subsequent telescopic expansive movement of said sleeve cylindrical housing relative to said trocar tubular housing is resisted.

10. The device of claim 4, wherein said means for selectively securing said sleeve cylindrical housing in said telescopically contracted position comprises: a snap groove defined around the exterior of one of said sleeve cylindrical housing and said trocar tubular housing, and flexible means carried by the other of said sleeve cylindrical housing and said trocar tubular housing, and movable into said snap groove when said sleeve cylindrical housing is in said telescopically contracted position, whereby subsequent telescopic expansive movement of said sleeve cylindrical housing relative to said trocar tubular housing is resisted.

11. The device of claim 1, wherein said means for selectively securing said sleeve cylindrical housing in said telescopically contracted position comprises: a snap groove defined around the exterior of said sleeve cylindrical housing, and flexible means carried by said trocar tubular housing movable to said snap groove when said sleeve cylindrical housing is in said telescopically contracted position, whereby subsequent telescopic expansive movement of said sleeve cylindrical housing relative to said trocar tubular housing is resisted.

12. The device of claim 2, wherein said means for selectively securing said sleeve cylindrical housing in said telescopically contracted position comprises: a snap groove defined around the exterior of said sleeve cylindrical housing, and flexible means carried by said trocar tubular housing movable to said snap groove when said sleeve cylindrical housing is in said telescopically contracted position, whereby subsequent telescopic expansive movement of said sleeve cylindrical housing relative to said trocar tubular housing is resisted.

13. The device of claim 3, wherein said means for selectively securing said sleeve cylindrical housing in said telescopically contracted position comprises: a snap groove defined around the exterior of said sleeve cylindrical housing, and flexible means carried by said trocar tubular housing movable to said snap groove when said sleeve cylindrical housing is in said telescopically contracted position, whereby subsequent telescopic expansive movement of said sleeve cylindrical housing relative to said trocar tubular housing is resisted.

14. The device of claim 4, wherein said means for selectively securing said sleeve cylindrical housing in said telescopically contracted position comprises: a snap groove defined around the exterior of said sleeve cylindrical housing, and flexible means carried by said trocar tubular housing movable to said snap groove when said sleeve cylindrical housing is in said telescopically contracted position, whereby subsequent telescopic expansive movement of said sleeve cylindrical housing relative to said trocar tubular housing is resisted.

15. A combination surgical trocar housing and selective reducer sleeve assembly, comprising: an elongated trocar tubular housing of a first internal diameter, having a first open end portion for positioning through a body wall, and a second opposite open end portion for introduction and removal of auxiliary surgical devices therethrough while said first open end portion is positioned through the body wall; a reducer sleeve assembly having first, second and subsequent members consecutively and concentrically introduceable through said second opposite open end portion of said trocar housing, the first of said members being positioned into said trocar housing, and the second and subsequent of said members being introduced into another of the members, said first member including a cylindrical housing of a second external diameter less than the said internal diameter of the trocar housing, and each subsequent member including a cylindrical housing of an external diameter less than the internal diameter of the respective member within which said respective subsequent member is introduced; means for placing each of the sleeve assembly members in a limited telescopically contracted position relative to one of said trocar housing and another of said reducer sleeve assembly members; and mechanical means for selectively securing a at least one of said sleeve cylindrical housings in said telescopically contracted position.

16. The device of claim 15 further including means for sealing the area defined by the outer diameter of the respective sleeve cylindrical housing and the internal diameter of each of said trocar housing immediate said second opposite end portion and each of said sleeve assembly members, to prevent fluid flow across said sealed area.

17. A surgical reducer sleeve assembly for introduction into an elongated trocar tubular housing of a first internal diameter, said trocar tubular housing having a first open end portion for positioning through a body wall and a second opposite end portion for introduction and removal of auxiliary surgical devices therethrough while said first open end portion is positioned through the body wall, said reducer sleeve assembly being concentrically introducible through said second opposite end portion of said trocar housing, said reducer sleeve assembly comprising: a cylindrical housing of a second external diameter less than the said internal diameter of the trocar housing said reducer sleeve assembly having a first inboard open end and a second outboard open end, said first and second open ends permitting introduction and removal of said auxiliary surgical devices into and out of said open ends of said assembly while said assembly is within said trocar housing; means for placing the sleeve cylindrical housing in a limited telescopically contracted position relative to said trocar housing; and mechanical means for selectively securing said sleeve cylindrical housing in said telescopically contracted position.

18. The device of claim 17 further including: means for sealing the area defined by the outer diameter of the sleeve cylindrical housing and the internal diameter of the trocar housing immediate said second opposite open end portion, to prevent fluid flow thereacross.

19. The device of claim 17 further including: means for sealing the area defined by the outer diameter of the sleeve cylindrical housing and the internal diameter of the trocar housing immediate said second opposite open end portion, to prevent fluid flow from the interior of said trocar tubular housing and through said second opposite open end.

20. The device of claim 18 or claim 13, said means for sealing comprising: a circumferentially extending conically shaped ring member on one of said sleeve cylindrical housing and said trocar tubular housing, and a companionly profiled sealing groove defined around the other of said sleeve cylindrical housing and said trocar tubular housing.

21. The device of claim 17, said cylindrical housing having a passageway therethrough communicating with the interior of said trocar tubular housing and terminating in an opening through the outboard most end of said sleeve cylindrical housing for receipt of auxiliary surgical device therethrough, and further including: a first seal means for sealing said opening, said first seal means being formed of resilient material having a concave curvature facing the first open end portion of said trocar tubular housing; a slit formed through the seal means to define first and second seal lips facing each other and placable in sealing relationship around the exterior of said sleeve housing as said sleeve housing is placed through said trocar tubular housing, said lips moving into sealing contact with one another when said sleeve housing is not therebetween to seal the said opening of said sleeve housing; and second seal means outboard of said first seal means for sealing around said sleeve housing as said sleeve housing is placed through said trocar tubular housing.

22. The device of claim 17 or claim 21, said sleeve cylindrical housing being further adapted to sealingly and latchingly receive a second cylindrical housing of a third exterior diameter less than the said interior diameter of said cylindrical housing.

23. The device of claim 17, wherein said means for selectively securing said sleeve cylindrical housing in said telescopically contracted position comprises: a snap groove defined around the exterior of one of said sleeve cylindrical housing and said trocar tubular housing, and flexible means carried by the other of said sleeve cylindrical housing and said trocar tubular housing, and movable into said snap groove when said sleeve cylindrical housing is in said telescopically contracted position, whereby subsequent telescopic expansive movement of said sleeve cylindrical housing relative to said trocar tubular housing is resisted.

24. The device of claim 18, wherein said means for selectively securing said sleeve cylindrical housing in said telescopically contracted position comprises: a snap groove defined around the exterior of one of said sleeve cylindrical housing and said trocar tubular housing, and flexible means carried by the other of said sleeve cylindrical housing and said trocar tubular cylindrical housing is in said telescopically contracted position, whereby subsequent telescopic expansive movement of said sleeve cylindrical housing relative to said trocar tubular housing is resisted.

25. The device of claim 19, wherein said means for selectively securing said sleeve cylindrical housing in said telescopically contracted position comprises: a snap groove defined around the exterior of one of said sleeve cylindrical housing and said trocar tubular housing, and flexible means carried by the other of said sleeve cylindrical housing and said trocar tubular housing, and movable into said snap groove when said sleeve cylindrical housing relative to said trocar tubular housing is resisted.

26. The device of claim 20, wherein said means for selectively securing said sleeve cylindrical housing in said telescopically contracted position comprises: a snap groove defined around the exterior of one of said sleeve cylindrical housing and said trocar tubular housing, and flexible means carried by the other of said sleeve cylindrical housing and said trocar tubular housing, and movable into said snap groove when said sleeve cylindrical housing is in said telescopically contracted position, whereby subsequent telescopic expansive movement of said sleeve cylindrical housing relative to said trocar tubular housing is resisted.

27. The device of claim 17, wherein said means for selectively securing said sleeve cylindrical housing in said telescopically contracted position comprises: a snap groove defined around the exterior of said sleeve cylindrical housing, and flexible means carried by said trocar tubular housing movable to said snap groove when said sleeve cylindrical housing is in said telescopically contracted position, whereby subsequent telescopic expansive movement of said sleeve cylindrical housing relative to said trocar tubular housing is resisted.

28. The device of claim 18, wherein said means for selectively securing said sleeve cylindrical housing in said telescopically contracted position comprises: a snap groove defined around the exterior of said sleeve cylindrical housing, and flexible means carried by said trocar tubular housing movable to said snap groove when said sleeve cylindrical housing is in said telescopically contracted position, whereby subsequent telescopic expansive movement of said sleeve cylindrical housing relative to said trocar tubular housing is resisted.

29. The device of claim 19, wherein said means for selectively securing said sleeve cylindrical housing in said telescopically contracted position comprises: a snap groove defined around the exterior of said sleeve cylindrical housing, and flexible means carried by said trocar tubular housing movable to said snap groove when said sleeve cylindrical housing is in said telescopically contracted position, whereby subsequent telescopic expansive movement of said sleeve cylindrical housing relative to said trocar tubular housing is resisted.

30. The device of claim 20, wherein said means for selectively securing said sleeve cylindrical housing in said telescopically contracted position comprises: a snap groove defined around the exterior of said sleeve cylindrical housing, and flexible means carried by said trocar tubular housing movable to said snap groove when said sleeve cylindrical housing is in said telescopically contracted position, whereby subsequent telescopic expansive movement of said sleeve cylindrical housing relative to said trocar tubular housing is resisted.

31. A combination surgical trocar housing and selective reducer sleeve assembly, comprising: an elongated trocar tubular housing of a first internal diameter, having a first open end portion for positioning through a body wall, and a second opposite open end portion for introduction and removal of auxiliary surgical devices therethrough while said first open end portion is positioned through the body wall; a reducer sleeve assembly having first, second and subsequent members consecutively and concentrically introducable through said second opposite open end portion of said trocar housing, the first of said members being positioned into said trocar housing, and the second subsequent of said members being introduced into another of the members, said first member including a cylindrical housing of a second external diameter less than the said internal diameter of the trocar housing, and each subsequent member including a cylindrical housing of an external diameter less than the internal diameter of the respective member within which said respective subsequent member is introduced; means for placing each of the sleeve assembly members in a limited telescopically contracted position relative to one of said trocar housing and another of said insert sleeve assembly members; and mechanical means for selectively securing a at least one of said sleeve cylindrical housings in said telescopically contracted position.

32. The device of claim 31 further including means for sealing the area defined by the outer diameter of the respective sleeve cylindrical housing and the internal diameter of each of said trocar housing immediate said second opposite end portion and each of said sleeve assembly members, to prevent fluid flow across said sealed area.

33. A combination surgical trocar housing and selective reducer sleeve assembly, comprising: an elongated trocar tubular housing of a first internal diameter, having a first open end portion for positioning through a body wall, and a second opposite open end portion for introduction and removal of auxiliary surgical devices therethrough while said first open end portion is positioned through the body wall; a reducer sleeve assembly concentrically introducible through said second opposite open end portion of said trocar housing and including a cylindrical housing of a second external diameter less than the said internal diameter of the trocar housing said reducer sleeve assembly having a first inboard open end and a second outboard open end, said first and second open ends permitting introduction and removal of said auxiliary surgical devices into and out of said open ends of said assembly while said assembly is within said trocar housing; and mechanical means for securing the sleeve cylindrical housing in a limited telescopically contracted position relative to said trocar housing.

34. A surgical reducer sleeve assembly for introduction into an elongated trocar tubular housing of a first internal diameter, said trocar tubular housing having a first open end portion for positioning through a body wall and a second opposite end portion for introduction and removal of auxiliary surgical devices therethrough while said first open end portion is positioned through the body wall, said reducer sleeve assembly being concentrically introducible through said second opposite end portion of said trocar housing, said reducer sleeve assembly comprising: a cylindrical housing of a second external diameter less than the said internal diameter of the trocar housing said reducer sleeve assembly having a first inboard open end and a second outboard open end, said first and second open ends permitting introduction and removal of said auxiliary surgical devices into and out of said open ends of said assembly while said assembly is within said trocar housing; and mechanical means for securing the sleeve cylindrical housing in a limited telescopically contracted position relative to said trocar housing.

35. A combination surgical trocar housing and selective reducer sleeve assembly, comprising: an elongated trocar tubular housing of a first internal diameter, having a first open end portion for positioning through a body wall, and a second opposite open end portion for introduction and removal of auxiliary surgical devices therethrough while said first open end portion is positioned through the body wall; a reducer sleeve assembly having first, second and subsequent members consecutively and concentrically introducable through said second opposite open end portion of said trocar housing, the first of said members being positioned into said trocar housing, and the second and subsequent of said members being introduced into another of the members, said first member including a cylindrical housing of a second external diameter less than the said internal diameter of the trocar housing, and each subsequent member including a cylindrical housing of an external diameter less than the internal diameter of the respective member within which said respective subsequent member is introduced; and mechanical means for securing at least one of the sleeve assembly members in a limited telescopically contracted position relative to one of said trocar housing and another of said reducer sleeve assembly members.

* * * * *